US010112152B2

(12) United States Patent
Serra et al.

(10) Patent No.: US 10,112,152 B2
(45) Date of Patent: Oct. 30, 2018

(54) PROTON CONDUCTING CERAMIC MEMBRANE

(71) Applicant: PROTIA AS, Oslo (NO)

(72) Inventors: Josè Manuel Serra, Valencia (ES); Sonia Escolástico, Gilet (ES)

(73) Assignee: PROTIA AS, Oslo (NO)

( * ) Notice: Subject to any disclaimer, the term of this patent is extended or adjusted under 35 U.S.C. 154(b) by 70 days.

(21) Appl. No.: 14/892,945

(22) PCT Filed: May 23, 2014

(86) PCT No.: PCT/EP2014/060708
§ 371 (c)(1),
(2) Date: Nov. 20, 2015

(87) PCT Pub. No.: WO2014/187978
PCT Pub. Date: Nov. 27, 2014

(65) Prior Publication Data
US 2016/0096151 A1   Apr. 7, 2016

(30) Foreign Application Priority Data

May 23, 2013 (GB) .................................. 1309336.4

(51) Int. Cl.
*B01D 53/22* (2006.01)
*B01D 67/00* (2006.01)
(Continued)

(52) U.S. Cl.
CPC ......... *B01D 71/024* (2013.01); *B01D 53/228* (2013.01); *B01D 67/0041* (2013.01);
(Continued)

(58) Field of Classification Search
CPC .. B01D 53/228; B01D 67/0041; B01D 69/12; B01D 71/024; C01G 37/00;
(Continued)

(56) References Cited

U.S. PATENT DOCUMENTS 6,037,514 A    3/2000  White et al.
6,620,320 B1 * 9/2003  Hying ................. B01D 53/228
                                                210/490
(Continued)

FOREIGN PATENT DOCUMENTS

DE    10 2010 029 645 A1   12/2011
WO        03/037490 A1     5/2003
(Continued)

OTHER PUBLICATIONS

International Search Report dated Sep. 18, 2014, issued in counterpart Application No. PCT/EP2014/060708 (4 pages).
(Continued)

*Primary Examiner* — Jason M Greene
(74) *Attorney, Agent, or Firm* — Westerman, Hattori, Daniels & Adrian, LLP

(57) ABSTRACT

A proton conducting ceramic membrane comprising a conducting layer, wherein said conducting layer comprises a mixture of a rare-earth tungstate as herein defined and a mixed metal oxide as herein defined. The invention also relates to a reactor comprising said membrane and the use of said membrane in a dehydrogenation process.

13 Claims, 9 Drawing Sheets

Schematic illustration of membrane operation of the composite membrane coated with a top porous electronic layer (dark grains = LSC and bright grains = LWO)

(51) Int. Cl.

| | |
|---|---|
| B01D 69/12 | (2006.01) |
| B01D 71/02 | (2006.01) |
| C07C 2/84 | (2006.01) |
| C04B 35/495 | (2006.01) |
| C01B 3/50 | (2006.01) |
| C01G 37/00 | (2006.01) |
| C04B 35/42 | (2006.01) |
| C01G 41/00 | (2006.01) |
| H01M 8/1246 | (2016.01) |

(52) U.S. Cl.
CPC .............. *B01D 69/12* (2013.01); *C01B 3/503* (2013.01); *C01B 3/505* (2013.01); *C01G 37/006* (2013.01); *C01G 41/00* (2013.01); *C01G 41/006* (2013.01); *C04B 35/42* (2013.01); *C04B 35/495* (2013.01); *C07C 2/84* (2013.01); *B01D 2053/221* (2013.01); *C04B 2235/32* (2013.01); *C04B 2235/3206* (2013.01); *C04B 2235/326* (2013.01); *C04B 2235/3208* (2013.01); *C04B 2235/3213* (2013.01); *C04B 2235/3215* (2013.01); *C04B 2235/3217* (2013.01); *C04B 2235/3224* (2013.01); *C04B 2235/3225* (2013.01); *C04B 2235/3227* (2013.01); *C04B 2235/3229* (2013.01); *C04B 2235/3232* (2013.01); *C04B 2235/3239* (2013.01); *C04B 2235/3241* (2013.01); *C04B 2235/3243* (2013.01); *C04B 2235/3256* (2013.01); *C04B 2235/3258* (2013.01); *C04B 2235/3262* (2013.01); *C04B 2235/3272* (2013.01); *C04B 2235/3275* (2013.01); *C04B 2235/3279* (2013.01); *C04B 2235/3286* (2013.01); *C04B 2235/449* (2013.01); *C04B 2235/5436* (2013.01); *C04B 2235/5445* (2013.01); *C04B 2235/785* (2013.01); *C04B 2235/786* (2013.01); *C04B 2235/80* (2013.01); *H01M 8/1246* (2013.01); *Y02E 60/525* (2013.01); *Y02P 70/56* (2015.11)

(58) Field of Classification Search
CPC ...... C01G 37/006; C01G 37/02; C01G 39/00; C01G 39/006; C01G 39/02; C01G 41/00; C01G 41/006; C01G 41/02; C04B 35/42; C04B 35/495; C04B 2235/3256; C04B 2235/3258; C07C 2/84; C01B 3/503; C01B 3/505

See application file for complete search history.

(56) References Cited

U.S. PATENT DOCUMENTS

| | | | |
|---|---|---|---|
| 2004/0241071 A1 | 12/2004 | Julsrud et al. | |
| 2005/0252853 A1* | 11/2005 | Berland | B01D 53/228 210/500.25 |
| 2006/0249461 A1* | 11/2006 | Luca | C01G 41/006 210/688 |
| 2006/0262839 A1 | 11/2006 | Tseng et al. | |
| 2007/0245897 A1* | 10/2007 | Besecker | B01D 53/228 96/11 |
| 2009/0136695 A1 | 5/2009 | Damani et al. | |
| 2012/0310027 A1* | 12/2012 | Kjolseth | C01B 3/26 585/654 |
| 2013/0216938 A1 | 8/2013 | Meulenberg et al. | |

FOREIGN PATENT DOCUMENTS

| | | | | |
|---|---|---|---|---|
| WO | 2007/087780 A2 | 8/2007 | | |
| WO | 2011/098525 A1 | 8/2011 | | |
| WO | WO 2011/098525 A1 * | 8/2011 | ............... | C01B 3/50 |
| WO | 2012/010386 A1 | 1/2012 | | |

OTHER PUBLICATIONS

Written Opinion dated dated Sep. 18, 2014, issued in counterpart Application No. PCT/EP2014/060708 (5 pages).

Yoshimura et al., "Electrical Conductivity of Solid Solutions in The System CeO2-La6WO12", Materials Research Bulletin, vol. 10, (1975) No. 9, pp. 983-988.

Shimura et al., "Proton Conduction in Non-Perovskite-Type Oxides At Elevated Temperatures", Solid State Ionics, vol. 143, (2001), pp. 117-123.

Haugsrud et al., "Effects of Protons and Acceptor Substitution on the Electrical Conductivity of La6WO12", J. Phys. Chem. Solids, vol. 69, (2008), No. 7, pp. 1758-1765.

Escolastico et al., "Preparation and Characterization of Nanocrystalline Mixed Proton-Electronic Conduction Materials Based on the System Ln6WO12", Chemical Matter, vol. 21, (2009), No. 14, pp. 3079-3089.

Solis et al., "La5.5WO12-d Characterization of Transport Properties Under Oxidizing Conditions: A Conductivity Relaxation Study", Journal of Physical Chemistry C, vol. 115, (2011), No. 22, pp. 11124-11131.

Escolastico et al., "Hydrogen Separation and Stability Study of Ceramic Membranes Based on the System Nd5LnWO12", International Journal of Hydrogen Energy, vol. 36, No. 18, (2011), pp. 11946-11954.

Solis et al., "Electrochemical Properties of Composite Fuel Cell Cathodes for La5.5WO12-d Proton Conducting Electrolytes", Journal of Materials Chemistry, vol. 22, No. 31, (2012), pp. 16051-16059.

Luo et al., "CO2-Stable and Cobalt-Free Dual-Phase Membrane for Oxygen Separation", Angewandte Chemie Int. Ed., 2011, vol. 50, pp. 759-763.

Zuo et al., "Composite Ni—Ba(Zr0.1Ce0.7Y0.2)O3 Membrane for Hydrogen Separation", Journal Power Sources, vol. 159, (2006), pp. 1291-1295.

Amsif et al., "Mo-Substituted lanthanum Tungstate La28_yW4+yO54+Fg: A Competitive Mixed Electron-Proton Conductor for Gas Separation Membrane Applications", Chemistry of Materials, vol. 24, No. 20, (2012), pp. 3868-3877.

Seeger et al., "Synthesis and Characterization of Nonsubstituted and Substituted Proton-Conducting La6_xWO12_y", Inorganic Chemistry, vol. 52, (2013), pp. 10375-10386.

Escolatico et al., "Study of Hydrogen Permeation in (La5/6Nd1/6)5.5WO12_g Membranes", Solid State Ionics, vol. 216, (2012), pp. 31-35.

Zayas-Rey et al., "Structural and Conducting Features of Niobium-Doped Lanthanum Tungstate, La27(W1_xNbx) 5O55.55-g", Chemistry of Materials, vol. 25, (2013), pp. 448-456.

Oishi et al., "Oxygen Nonstoichiometry of B-site Doped LaCRO3", Solid State Ionics, vol. 178, (2007), pp. 307-312.

Baker, R. T. et al., "Activity and Deactivation of La0.8Ca0.2CrO3 in Dry Methane Using Temperature-Programmed Techniques", Appl. Catal. A: General, vol. 126, (1995), 297-317.

Sfeir et al., "Lanthanum Chromite Based Catalysts for Oxidation of Methane Directly on SOFC Anodes", Journal of Catalysis, vol. 202, (2001), pp. 229-244.

Koc et al., "Electrical and Thermal Transport Properties of (La,Ca)(Cr,Co)O3", Journal of the European Ceramic Society, vol. 15, (1995), pp. 867-874.

Magraso et al., "New Crystal Structure and Characterization of lanthanum Tungstate of "La6WO12" Prepared by Freeze-Drying Synthesis", Dalton Transactions, 2009, pp. 10273-10283.

Mukasyan et al, "Perovskite membranes by Aqueous Combustion Synthesis: Synthesis and Properties", Separation and Purification Technology, 2001, vol. 25, pp. 117-126.

Park et al, "Effect of Surface Modification of Ba0.5Sr0.5Co0.8Fe0.2O3-b Membrane for Oxygen Separation", Energy Procedia, vol. 4, (2011), pp. 653-658.

Balachandran, et al., "Hydrogen Separation by Dense Cermet Membranes", Fuel, vol. 85, (2006), pp. 150-155.

Mundschau et al., "Dense Inorganic Membranes For Production of Hydrogen From Methane and Coal With Carbon Dioxide Sequestration", Catalysis Today, vol. 118, (2006), pp. 12-23.

(56) References Cited

OTHER PUBLICATIONS

Hamakawa et al., "Synthesis and Hydrogen Permeation Properties of Membranes Based on Dense SrCe0.95Yb0.05O3-x Thin Films", Solid State Ionics, vol. 48, (2002), pp. 71-81.

Hausgrud et al., "Mixed Ionic and Electronic Conductivity of Undoped and Acceptor-Doped Er6WO12", Journal of Electrochemical Society, 2007, vol. 154, No. 1, B77-B81.

Vert et al., "Redox Stability and Electrochemical Study of Nickey Doped Chromites as Anodes for Hx/CH4-Fueled Solid Oxide Fuel Cells", Applied Catalysis B: Environmental, 115-116, (2012), pp. 346-356.

Hancke et al., "Thermogravimetric Relaxation Study of the Proton Conductor lanthanum Tungstate, La28-xW4+xO54+oV2-o, x=0.85", International Journal of Hydrogen Energy, (2012), pp. 8043-8050.

J. M. Serra, et al., "Ceramic Hydrogen-Permeable Membranes made of Mixed Proton-Electronic Conducting Materials based on the system Ln6WO12", Proceedings of 2009 E-MRS Fall Meeting, Sep. 14-18, Warsaw, p. 140.

Thomas Kiefer PhD Dissertation thesis, (2007), FZ Jülich—Ruhr University Bochum (Germany).

Serra et al., "Hydrogen Permeation Through La5.5 WO12 Membranes", Presented at 10th CMCee—International Symposium on Ceramic Materials and Components for Energy and Environmental Applications, pp. 38-39, May 20-23, 2012, Dresden (Germany).

\* cited by examiner

XRD patterns of the starting powders and the final composite membrane

SEM image and EDX analysis of a 50/50 composite membrane

SEM images of a 50/50 composite membrane and a LSC membrane

SEM images of a 50/50 composite membrane with the top electronic coating

Schematic illustration of membrane operation of the composite membrane coated with a top porous electronic layer (dark grains = LSC and bright grains = LWO)

Total conductivity of LWO, LSC and different LWO-LSC composites as function of inverse temperature measured under four different reducing atmospheres: dry $H_2$, $H_2+H_2O$ (2.5% vol.), dry $D_2$ and $D_2+D_2O$ (2.5% vol.) for LWO, LSC and LWO+LSC Hydrogen separation flow obtained with three different kinds of membranes: all-LWO (0.7mm-thick), composite 50/50 LWO/LSC (0.7 and 0.4mm-thick) and composite 20/80 LWO/LSC (0.45 thick)

Hydrogen flux as a function of temperature using wet Ar and wet 1%$O_2$ diluted with Ar as sweep gas "Low" temperature permeation test using a 0.4mm-thick membrane. Best composite composition Stability on stream in $CO_2$ environment (0.7mm-thick 50/50 composite membrane): Hydrogen flow as function of time using 15% $CO_2$-85% Ar as sweep gas and 50%He-50% $H_2$ as feed gas at 800°C. Both sides of membrane were humidified TG measurements of LWO+LSC cer-cer in 5% $CO_2$ in Ar.
TG data for $BaCe_{0.9}Yb_{0.1}O_{3-\delta}$ were plotted for comparison Hydrogen separation flow obtained with three different kinds of membranes: all-LWO (0.7mm-thick), composite 50/50 LWO/LSC (variable thickness) with Pt-coating, LSC-coating and uncoated.

PROTON CONDUCTING CERAMIC MEMBRANE

This invention relates to a proton conducting ceramic membrane which can be used to enable dehydrogenation reactions, in particular, alkane to alkene transformation and steam reforming of alkanes. More specifically, the invention relates to the use of a combination of two mixed metal oxides in the manufacture of a proton conducting ceramic membrane.

BACKGROUND

With depletion of global liquid petroleum reserves, natural gas, containing primarily methane, is expected to be one of the main resources for the production of liquid fuels. However, direct dehydrogenation of light alkanes like methane and ethane to more valuable olefins remains challenging.

For ethane to olefin production, commercial processes include steam cracking and catalytic dehydrogenation, and recently there has also been renewed interest in oxidative dehydrogenation.

Oxidative dehydrogenation offers direct conversion from alkanes into valuable chemicals. By adding oxygen discretely through either porous or dense oxygen permeable membranes, the alkane to oxygen ratio can be kept high, promoting high $C_{2+}$ selectivity.

A somewhat less investigated route for alkane conversion to fuels is through non-oxidative reactions. Here, using methane as an example, a coupling/dimerization/pyrolysis (hereafter denoted coupling) reaction takes place on the methane side of a reactor with hydrogen permeating through a membrane in the form of protons onto the oxygen side, where it reacts with oxygen to form water.

Oxygen is not present in the methane coupling compartment, avoiding the oxidation of methane. A high $C_{2+}$ selectivity may thus be expected. This is a highly efficient way to make olefins from alkanes compared to existing technologies.

It has been shown theoretically that removal of hydrogen during coupling promotes homogeneous reaction pathways and shifts the equilibrium towards the product side. A hydrogen selective membrane in the process stream should therefore increase the yield considerably. The removal of hydrogen can be achieved using hydrogen permeable membranes.

Several such membranes exist. Catalytic dehydrogenation of ethane in a hydrogen membrane reactor has been investigated using a microporous silica membrane and a 5.0 wt. % $Cr_2O_3/\gamma$-$Al_2O_3$ catalyst prepared by incipient wetness impregnation of a $\gamma$-$Al_2O_3$ support.

A Pd—Ag composite membrane supported on porous stainless steel prepared by electroless plating has been used in a catalytic membrane reactor utilizing a Ru—Mo/HZSM-5 catalyst.

Using the ceramic mixed proton-electron conductor $SrCe_{0.95}Yb_{0.05}O_{3-\delta}$ a membrane configuration and also a co-generative fuel cell has been developed towards methane coupling.

There are problems with all these solutions however. Microporous membranes suffer from being fragile and difficult to make. Their hydrogen selectivity is also poor.

Pd—Ag membranes are inherently very expensive and whilst complex membranes have been formed in an attempt to minimise expensive metal content, there remains a desire to have a much simpler membrane. The catalytic activity of these metals towards formation of coke is also a considerable problem if these materials are used in a catalytic membrane reactor.

Ceramic oxides offer a more attractive option therefore. However, even initiatives using ceramic proton conducting materials have serious limitations. The prior art ceramic oxides are based on Ba- and Sr-based perovskites. These compounds are basic and are prone to react with $CO_2$ and $H_2S/SO_2/SO_3$ at moderate temperature and $H_2O$ at low temperatures to form alkaline earth carbonates, sulphates and hydroxides, respectively. Consequently, a decrease in conductivity is observed.

These reactions are prohibitive if using any carbon-containing feed gas as the impurities in the gas react with the membrane. Moreover, the reaction with carbon dioxide precludes the use of air in a reactor meaning expensive inert gases have to be used. Moreover, the electrical and mechanical properties of these materials become poor due to the formation of carbonates and hydroxides.

The use of mixed metal tungstates offers an ideal solution to this problem. These materials are stable in the presence of carbon dioxide and acidic gases in general making them usable in the presence of air. This also means the membranes can be used in the presence of hydrocarbon feed gases.

Mixed metal tungstates are not themselves new. In Solid State Ionics, 143 (2001), 117-123, the authors investigate the proton conducting properties of lanthanum tungstates. The present inventors have realised that these proton conducting materials, as opposed to the numerous other proton conducting materials known, offer the most attractive properties for use in dehydrogenation reactions, in particular of alkanes to alkenes (olefins/aromatics).

Ceramic materials selected from a group of rare-earth tungstates, often in literature denoted with formulas $Ln_{6-x}WO_{12-\delta}$, where Ln refers to lanthanides or rare earth elements, have been known to have proton conducting properties for some time (Yoshimura et al. Materials Research Bulletin 10 (1975) (9) 983) but have received increasing interest after being examined by Shimura et al. and later Haugsrud et al. (Shimura et al. Solid State Ionics 143 (2001) 117, Haugsrud et al. J. Phys. Chem. Solids 69 (2008) (7) 1758). Rare-earth tungstates exhibit highest proton conductivity when nominally undoped, a characteristic that sets them apart from the more well characterized proton conductors of pervoskite systems such as acceptor doped $SrCeO_3$ or $BaCeO_3$. Rare-earth tungstates of formula $Ln_{6-x}WO_{12-\delta}$ are known to exhibit mixed proton and electron conductivity (n-type conductivity) in reducing atmospheres and mixed proton and electron hole conductivity (p-type conductivity) under oxidizing conditions (Escolastico et al. Chem. Mat 21 (2009) (14) 3079 and Haugsrud et al. J. Phys. Chem. Solids 69 (2008) (7) 1758). An increase in conductivity with increasing reducing or oxidizing conditions indicates dominating n- and p-type conduction respectively.

Hence, rare-earth tungstates are today considered by many to be a promising candidate for hydrogen separation membranes where they are solely used under reducing conditions and for electrode materials in proton conducting solid oxide fuel cells (see, for example, Haugsrud et al. J. Phys. Chem. Solids 69 (2008) (7) 1758, Escolastico et al. Chem. Mat. 21 (2009) (14) 3079; Solis et al. Journal of Physical Chemistry C 115 (2011) (22) 11124; Escolastico et al. International Journal of Hydrogen Energy 36(18) (2011) 11946-11954; Solis et al Journal of Materials Chemistry 22 (31) (2012) 16051-16059) where the n-type conduction is utilized in a membrane and either the n-type or the p-type partial conduction is utilized in the anode or cathode electrode, respectively.

The use of n-type and p-type conduction in a ceramic membrane comprising rare-earth tungstates has been reported. This is achieved by way of electron conduction (n-type) in one portion of the ceramic membrane and by way of electron hole conduction (p-type) in another portion of the membrane, enabling the transport of hydrogen, dissociated as protons and electrons/electron holes, across the membrane. Consequently, these types of ceramic membranes comprise at least two layers, each comprising a different tungstate material.

Despite the attractive proton conductivity properties of these known rare-earth tungstates, the n-type electronic conductivity, especially at temperatures below 750° C., appears to limit the hydrogen permeation process, especially in $La_{6-x}WO_{12-\delta}$ (LWO) which presents one of the highest protonic conductivity of the $Ln_{6-x}WO_{12-\delta}$ series. There remains therefore a need to develop new membrane materials which maintain the optimum proton conductivity properties and stability, especially in $CO_2$-rich environments, of the tungstates but which also overcome the problems associated with the poor electronic conductivity of these membranes.

The present inventors suggest the use of a combination of two mixed metal oxides in the manufacture of a proton conducting ceramic membrane. One of those mixed metal oxides is preferably based on a lanthanum tungstate.

The successful synthesis of doped $Ln_6W_{1.1}O_{12-\delta}$ compounds as single phase materials (defective fluorite) has been reported by Escolastico et al PhD Dissertation thesis, 2013; J. M. Serra, S. Escolástico, M. Ivanova, W. Meulenberg, J. Seeger, C. Solis, Hydrogen permeation through $La_{5.5}WO_{12}$ membranes presented at $10^{th}$ CMCee—International Symposium on ceramic materials and components for energy and environmental applications, 20-23 May 2012, Dresden (Germany). These compositions comprised $(Ln_{1-x}A_x)_6W_{1.1}O_{12-\delta}$ compounds, where A=lanthanides and/or alkali-earths, and, especially, $(Ln_{1-x}A_x)_6(W_{1-y}B_y)_{1.1}O_{12-\delta}$ where x=0.1, 0.5, 1 and B=Mo, Re, Cr, Nb, U, among others. The preparation was carried out principally by a sol-gel and pyrolysis method. Complete electrochemical conductivity measurements have been carried out for most of them, making special emphasis on the promotion of n-type conductivity in reducing gas environments and p-type conductivity in oxidizing gas environments.

Some examples of the tested samples: $Nd_5LaW_{1.1}O_{12-\delta}$, $Nd_5CeW_{1.1}O_{12-\delta}$, $Nd_5PrW_{1.1}O_{12-\delta}$, $Nd_5EuW_{1.1}O_{12-\delta}$, $Nd_5TbW_{1.1}O_{12-\delta}$, $Nd_5SmW_{1.1}O_{12-\delta}$, and, $Nd_6WMo_{0.1}O_{12-\delta}$, $Nd_6W_{0.6}Mo_{0.5}O_{12-\delta}$, $Nd_6WRe_{0.1}O_{12-\delta}$, $Nd_6W_{0.6}Re_{0.5}O_{12-\delta}$, $Nd_6WU_{0.1}O_{12-\delta}$, $Nd_6W_{0.6}U_{0.5}O_{12-\delta}$, $Nd_6WCr_{0.1}O_{12-\delta}$, $Nd_6W_{0.6}Cr_{0.5}O_{12-\delta}$, $Nd_6WNb_{0.1}O_{12-\delta}$ and $Nd_6W_{0.6}Nb_{0.5}O_{12-\delta}$. Similar doped compositions for $La_{5.4}WO_{12-\delta}$ doped with Nd, Ce, Tb, Y, Mo, Re and Ir are available in Seeger et al. Inorganic Chemistry 52 (2013) 10375-10386, Amsif et at. Chemistry of materials 24 (20) (2012) 3868-3877; Escolatico et al Solid State Ionics 216 (2012 31-35); and Zayas-Rey et al. Chemistry of Materials 25 (2013) 448-456.

Two general approaches are known in the art to be of value for increasing electronic conductivity in tungstates, (a) selective doping of the defective fluorite structure; and (b) "physical" mixing with a good electronic conducting phase. Approach (b) has been applied broadly in oxygen transport membranes (Angew. Chem. Int. Ed. 2011, 50, 759-763) and in hydrogen transport membranes (J. Power Sources 159 (2006) 1291-1295), the latter case involving blending the proton conductor with metals.

The present inventors have surprisingly found that blending a rare-earth tungstate (LWO) with a mixed metal oxide in a conducting layer makes it possible to substantially increase the "overall" ambipolar conductivity of the material. By having a balanced proportion of the LWO and mixed metal oxide phases, the hydrogen permeation flux of the LWO can be increased up to 5-fold when compared to single material membranes. Best results are obtained when the two phases are mixed as powders with grain sizes of less than a few μm. This maximises the electronic conductance effect, as well as the promotion of grain boundary effects.

Also of interest is separation of hydrogen from steam reformed natural gas. The membranes dissolve hydrogen gas as protons and electrons. The production of hydrogen from natural gas by steam reforming is a well-known art. The reaction is favoured by high temperature. By extracting hydrogen by means of a hydrogen membrane, the steam reforming reaction is shifted to the right and more hydrogen is produced.

The possibility of using a hydrogen permeable membrane in steam reforming has been investigated earlier as described in US 2004/0241071. One membrane composition utilized is a single phase of the mixed metal oxide used in the present invention. The material suffers from low proton conductivity at operating temperatures, however, and has not been proven commercially.

SUMMARY OF INVENTION

Thus, viewed from one aspect the invention provides a proton conducting ceramic membrane comprising a conducting layer, wherein said conducting layer comprises a mixture of:

(i) a rare-earth tungstate of formula (I)

$$(Ln_{z1}Dp_{z2})_a W_{b-c} M1_c O_{12-y} \quad (I)$$

wherein
Ln is Y, an element numbered 57 to 71, or a mixture thereof;
Dp is Y or an element numbered 57 to 71 of the periodic table different from Ln;
Z1 is 0.5 to 1;
Z2 is 0.5 to 0;
M1 is a metal selected from the group consisting of Mo, Re, V, Cr, Nb, U and Mn, or a mixture thereof;
the molar ratio of a:b is 4.8 to 6, preferably 5.3 to 6; c is 0 to (0.5*b); and
y is a number such that formula (I) is uncharged, e.g. y is 0≤y≤1.8; and
(ii) a mixed metal oxide selected from the group consisting of
(a) a mixed metal oxide of formula (II)

$$Ln_{e-d} M3_d Cr_{1-f} M2_f O_{3-x} \quad (II)$$

wherein
Ln is Y, an element numbered 57 to 71, or a mixture thereof;
M3 is a metal selected from Ca, Sr or Ba;
M2 is a metal selected from the group consisting of Al, Ga, Co, Ti, Mg, Mn, Fe, Ni, Y, Sc, Yb and Lu, or a mixture thereof; preferably Al, Ga, Mg, Mn, Fe, Ni, Y, Sc, Yb and Lu, or a mixture thereof;
e is 0.95 to 1;
d is 0.4 to 0.01;
f is 0 to 0.5; and
x is a number such that formula (II) is uncharged, e.g. x is 0≤x≤0.5;

(b) a mixed metal oxide of formula (III) different to that of formula (I)

$$(Ln_{z1}Dp_{z2})_a W_{b-c}M1_c O_{12-y} \quad (III)$$

wherein Ln is Y or an element numbered 57 to 71, or a mixture thereof;
Dp is Y or an element numbered 57 to 71 of the periodic table different from Ln;
the molar ratio of a:b is 4.8 to 6, preferably 5.3 to 6;
Z1 is 0.5 to 1;
Z2 is 0.5 to 0; and
M1 is a metal selected from the group consisting of Mo, Re, V, Cr, Nb, U and Mn, or a mixture thereof;
c is 0 to (0.5*b); and
y is a number such that formula (III) is uncharged, e.g. y is $0 \le y \le 1.8$; or
(c) a spinel mixed metal oxide of formula (IV)

$$M4M5_g O_{4-y} \quad (IV)$$

wherein
M5 is a metal selected from the group consisting of Al, Cr, Mn, Fe, Ti, Cu and Si or mixture thereof; preferably Al, Cr, Mn, Fe, Ti and Si or mixture thereof;
M4 is a metal selected from the group consisting of Ni, Fe, Mg, Zn, Cu, Mn, Co and Ti or a mixture thereof; preferably Ni, Fe, Mg, Zn, Cu, Mn and Ti or a mixture thereof;
g is 1.5 to 2; and
y is a number such that formula (IV) is uncharged, e.g. y is $0 \le y \le 0.5$.

In a preferable embodiment, the membrane of the invention is coated on both sides with a porous electron conducting coating or a dense hydrogen permeable coating, wherein said coating preferably comprises a single phase material selected from a metal, metal-based alloy or ceramic compound, such as Pd, $Mo_2C$ or Pd-alloy (PdAg). It is also preferred if the particles of this coating are catalytic towards hydrogen dissolution or evolution.

Viewed from another aspect the invention provides a reactor comprising a first zone comprising a dehydrogenation catalyst and a second zone separated from said first zone by a proton conducting membrane as hereinbefore described.

Viewed from another aspect the invention provides the use of a proton conducting membrane as hereinbefore defined in a dehydrogenation process.

Viewed from another aspect the invention provides a process for the dehydrogenation of substance, e.g. an alkane, comprising introducing said substance into the first zone of a reactor as hereinbefore defined to thereby dehydrogenate said substance;
allowing hydrogen formed during said dehydrogenation to pass through said proton conducting membrane into said second zone;
introducing a purge gas into said second zone, preferably to react with the hydrogen; or
applying reduced pressure in said second zone to thus remove hydrogen from said second zone.

DETAILED DESCRIPTION OF THE INVENTION

The hydrogen permeable membrane of the current invention comprises a conducting layer comprising a mixture of a rare-earth tungstate and a mixed metal oxide.

In all embodiments it is preferred if all the components of the conducting layer have electron conductivity as well as proton conductivity.

Rare-Earth Tungstate

The rare-earth tungstate (LWO) preferably has the general formula (I)

$$(Ln_{z1}Dp_{z2})_a W_{b-c}M1_c O_{12-y} \quad (I)$$

wherein
Ln is Y, an element numbered 57 to 71, or a mixture thereof;
Dp is Y or an element numbered 57 to 71 of the periodic table different from Ln;
Z1 is 0.5 to 1;
Z2 is 0.5 to 0;
M1 is a metal selected from the group consisting of Mo, Re, V, Cr, Nb, U and Mn, or a mixture thereof;
the molar ratio of a:b is 4.8 to 6, preferably 5.3 to 6;
c is 0 to (0.5*b); and
y is a number such that formula (I) is uncharged, e.g. y is $0 \le y \le 1.8$.

The rare-earth tungstate of the invention may be doped at the W site. Preferably, the rare-earth tungstate should not be doped at the Ln site.

It is preferred if the ratio of Ln to W (i.e. the ratio of a to b) is in the range 5.3 to 6, preferably 5.5 to 5.8, especially 5.6 to 5.7. In this embodiment therefore one or both of the Ln or W sites in the rare-earth tungstate may by stoichiometric or non stoichiometric. The stoichiometric oxide is $Ln_6WO_{12}$.

It will be appreciated that the value of y is intrinsically linked to the amounts of Ln, W and M1 present. Depending on the oxidation state of the Ln ion and the amount of W and M1 present, the value of y required to balance the formula can be found. This value ensures therefore that the rare-earth tungstate is uncharged. The subscript y is preferably in the range 0 to 0.75, preferably 0.1 to 0.75, especially 0.25 to 0.75, most especially 0.5 to 0.75

It is within the scope of the invention for the y group to be a negative number, symbolising therefore a compound with more than 1 equivalent of W.

Preferably the ratio of Ln/W and subscript "y" are related so that the compound of formula (I) is uncharged for a $Ln^{3+}$ ion, $W^{6+}$ ion and $O^{2-}$ ion.

M1 can substitute for up to half the amount of W and hence c can be up to 0.5*b. The ratio of Ln to W+M1 must be 4.8 to 6, i.e. the ratio a to [(b−c)+c] must be 4.8 to 6. It will be appreciated therefore that this reduces to a:b.

Preferably, c is 0.3 to 0.5*b, i.e. 30 to 50 mol % of W is exchanged for M1. The presence of the M1 will increase the electronic conductivity of the material. In an alternative embodiment M1 is absent.

Ln is preferably Y or an element numbered 57 to 71 or a mixture thereof. By a mixture thereof is meant that the Ln contribution to the oxide can be formed by two or more different Ln ions, e.g. La and Nd or Nd and Ce. Ln is preferably La, Y, Tb, Nd, Gd, Er, Ce, Pr and Eu. Ideally, Ln is La, Nd, Ce, Gd, Pr and Eu. The metal ion Ln is preferably La or Nd.

In a preferred embodiment Ln represents a mixture of two Ln ions where one is Nd.

Ln is preferably in the 3+ oxidation state.
The W ion is in the 6+ oxidation state.
The M1 ion is preferably in the 6+ oxidation state.
Most preferably M1 is Mo.
A preferred rare earth tungstate is therefore of formula (I')

$$La_a W_{b-c} Mo_c O_{12-y} \quad (I'),$$

e.g. $La_a W_b O_{12-y}$ (I'')

with variables as hereinbefore defined.

Preferred compositions are: $Nd_5LaW_{1.1}O_{12-\delta}$, $Nd_5CeW_{1.1}O_{12-\delta}$, $Nd_5PrW_{1.1}O_{12-\delta}$, $Nd_5EuW_{1.1}O_{12-\delta}$, $Nd_5TbW_{1.1}O_{12-\delta}$, $Nd_5SmW_{1.1}O_{12-\delta}$, $Nd_6WMo_{0.1}O_{12-\delta}$, $Nd_6W_{0.6}Mo_{0.5}O_{12-\delta}$, $Nd_6WRe_{0.1}O_{12-\delta}$, $Nd_6W_{0.6}Re_{0.5}O_{12-\delta}$, $Nd_6WU_{0.1}O_{12-\delta}$, $Nd_6W_{0.6}U_{0.5}O_{12-\delta}$, $Nd_6WCr_{0.1}O_{12-\delta}$, $Nd_6W_{0.6}Cr_{0.5}O_{12-\delta}$, $Nd_6WNb_{0.1}O_{12-\delta}$ and $Nd_6W_{0.6}Nb_{0.5}O_{12-\delta}$ (e.g. see Escolastico et al. International Journal of Hydrogen Energy 36 (2011) 11124-11131).

Similar doped compositions for $La_{5.4}WO_{12-\delta}$ doped with Nd, Ce, Tb, Y, Mo and Re are available in Seeger et al. Inorganic Chemistry 52 (2013) 10375-10386, and Zayas-Rey et al. Chemistry of Materials 25 (2013) 448-456.

Mixed Metal Oxide

In a first embodiment, the rare-earth tungstate of formula (I) is combined with a mixed metal oxide of Formula (II). The mixed metal oxide of Formula (II) is a lanthanum chromate and can be doped on the Ln site and the Cr site.

$$Ln_{e-d}M3_dCr_{1-f}M2_fO_{3-x} \tag{II}$$

wherein
Ln is Y, an element numbered 57 to 71, or a mixture thereof;
M3 is a metal selected from Ca, Sr or Ba;
M2 is a metal selected from the group consisting of Al, Ga, Mg, Mn, Fe, Ni, Y, Sc, Yb and Lu, or a mixture thereof;
e is 0.95 to 1;
d is 0.4 to 0.01;
f is 0 to 0.5; and
x is a number such that formula (II) is uncharged, e.g. x is $0 \leq x \leq 0.5$.

It will be appreciated that the value of x in formula (II) is intrinsically linked to the amounts of Ln, M3, M2 and Cr present. Depending on the oxidation state of the Ln ion and the amount and oxidation state of the Cr present and any dopants, the value of x required to balance the formula can be found. This value ensures therefore that the mixed metal oxide is uncharged.

Preferably the ratio of Ln/Cr and subscript "x" are related so that the compound of formula (I) is uncharged for a $Ln^{3}$ ion, $Cr^{3+}$ ion and $O^{2-}$ ion.

M2 can substitute for up to half the amount of Cr and hence f can be up to 0.5. In a further embodiment M2 is a metal selected from the group consisting of Al, Ga, Co, Ti, Mg, Mn, Fe, Ni, Y, Sc, Yb and Lu, or a mixture thereof, preferably Al, Ga, Mg, Mn, Fe, Ni, Y, Sc, Yb and Lu, or a mixture thereof. In a preferred embodiment M2 is Ni, Co, Fe, Ti, Mg or Mn, preferably Ni, Fe, Mg, or Mn. It is preferred however if M2 is absent. Thus preferred compounds of formula (II) are:

$$Ln_{e-d}M3_dCrO_{3-x} \tag{II'}$$

with variables as hereinbefore defined.
Preferably d is 0.01 to 0.2, such as 0.15.
Ln is preferably Y or an element numbered 57 to 71 or a mixture of such elements. Ln is preferably La, Y, Tb, Nd, Gd, Er, Ce, Pr and Eu. Ideally, Ln is La, Nd, Gd, Ce, Pr and Eu or a mixture thereof. The metal ion Ln is preferably La.
Ln is preferably in the 3+ oxidation state.
The Cr ion is in the 3+ oxidation state.
Preferred compositions are: $LaCrO_{0.9}Ni_{0.1}O_{3-\delta}$, $LaCr_{0.9}Co_{0.1}O_{3-\delta}$, $LaCr_{0.9}Fe_{0.1}O_{3-\delta}$, $LaCr_{0.9}Ti_{0.1}O_{3-\delta}$, $La_{0.8}Ca_{0.2}CrO_3$ and $La_{0.8}Ca_{0.2}Cr_{0.9}.(Co, Ni)_{0.1}O_3$, $LaCr_{0.9}Mg_{0.1}O_3$, $LaCr_{0.9}Mn_{0.1}O_3$, $La_{0.85}Ca_{0.15}Cr_{0.9}Mg_{0.1}O_3$, $La_{0.85}Sr_{0.15}CrO_3$, $La_{0.85}Sr_{0.15}Cr_{0.9}Mg_{0.1}O_3$ as reported in Oishi et al. Solid State Ionics 178 (2007) 307-312, Baker, R. T., and Metcalfe, I. S., *Appl. Catal. A: General.* 126, 297 (1995), Sfeir et al Journal of Catalysis 202 (2001) 229-244 and Koc et al Journal of the European Ceramic Society 15 (1995) 867-874 and the $(La,Ca)(Cr,Co)O_3$ system.

In a further embodiment, the rare-earth tungstate of formula (I) is combined with a mixed metal oxide of formula (III). The mixed metal oxide of Formula (III) is a rare-earth tungstate and may be doped on the Ln site or both the Ln and W sites.

$$(Ln_{z1}Dp_{z2})_aW_{b-c}M1_cO_{12-y} \tag{III}$$

wherein Ln is Y or an element numbered 57 to 71, or a mixture thereof;
Dp is Y or an element numbered 57 to 71 of the periodic table different from Ln; the molar ratio of a:b is 4.8 to 6, preferably 5.3 to 6;
Z1 is 0.5 to 1;
Z2 is 0.5 to 0; and
M1 is a metal selected from the groups consisting of Mo, Re, V, Cr, Nb, U and Mn, or a mixture thereof;
c is 0 to (0.5*b); and
y is a number such that formula (III) is uncharged, e.g. y is $0 \leq y \leq 1.8$.

The preferred values for a, b, c and y are as above for the rare-earth tungstate of formula (I). The preferred embodiments for Ln and M1 are also as for the rare-earth tungstate of formula (I).

Dp is preferably Sm or Nd. Preferably, z2 is 0.01 to 0.2, such as 0.15.

It is again preferred if M1 is absent and hence preferred compounds are of formula (III'):

$$(Ln_{z1}Dp_{z2})_aW_bO_{12-y} \tag{III'}$$

with variables as hereinbefore defined.

It is preferred if the compounds of formula (III) exhibit predominantly electronic conductivity.

In a further embodiment, the rare-earth tungstate of formula (I) is combined with a spinel mixed metal oxide of formula (IV).

$$M4M5_gO_{4-y} \tag{IV}$$

wherein
M5 is a metal selected from the group consisting of Al, Cr, Mn, Fe, Ti and Si or mixture thereof;
M4 is a metal selected from the group consisting of Ni, Fe, Mg, Zn, Cu, Mn and Ti or a mixture thereof;
g is 1.5 to 2; and
y is a number such that formula (IV) is uncharged, e.g. y is $0 \leq y \leq 0.5$.

It will be appreciated that M4 and M5 cannot generally both represent the same ion although ions of the same metal in a different oxidation state might be present such as $Fe_3O_4$.

Preferred spinels are based on $CrO_4^{2-}$ ions, such as $FeCrO_4$.

In a further embodiment, the rare-earth tungstate of formula (I) is combined with a mixture of two or more of the mixed metal oxides of formulae (II), (III) and (IV).

In an alternative embodiment M5 is a metal selected from the group consisting of Al, Co, Cu, Cr, Mn, Fe, Ti and Si or mixture thereof.

In an alternative embodiment M4 is a metal selected from the group consisting of Ni, Fe, Mg, Zn, Co, Cu, Mn and Ti or a mixture thereof.

Preferred compositions are: $CuMn_{1.9}Fe_{0.1}O_4$, $MnCo_2O_4$, $MnCo_{1.9}Fe_{0.1}O_4$, and $FeMn_2O_4$ reported in for instance Thomas Kiefer PhD Dissertation thesis (2007), FZ Jülich-Ruhr University Bochum (Germany).

Synthesis

The rare-earth tungstates and mixed metal oxides of the invention can be prepared by solid state reaction using appropriate starting materials. Calcination at temperatures of 1200° C. or more allows formation of the oxide. Sintering at temperatures of 1500° C. or more allows formation of dense components of the oxide.

More recently, the rare-earth tungstates and mixed metal oxides of formula (III) of the invention have been manufactured using freeze drying synthesis, such as that described in Dalton Trans 2009, 10273-10283.

The rare-earth tungstates and mixed metal oxides of formula (III) of the invention may also been manufactured by a spray pyrolysis route. Stable aqueous solutions of the precursors (Ln and W) are standardized by thermogravimetry and mixed to provide the desired stoichiometry. The solutions are then spray pyrolysed. The atomized solution is decomposed in the hot zone of the furnace (850° C.) and a homogeneous metal oxide mixture is obtained. The as-prepared powders can then be calcined in air followed by ball milling in 100% ethanol for 24 hours, dried in a rotavapor and sieved at 250 µm. Different calcination processing can be used, from 600-900° C., preferably 700-800° C. This is a more favourable route for the manufacture of the tungstates of the invention when used as the membrane.

It is thus favourable to use spray pyrolysed powder for membrane formation and solid state reaction powder as a support material. This forms a further aspect of the invention.

In Chem Matter, 2009, 21, 3079-3089, a sol-gel complexation synthesis method is described for forming lanthanum tungstates. The art therefore enables the formation of the mixed metal oxides of the invention and any convenient technique can be used.

In order to introduce dopants such as Mo ions into the mixed metal oxides of the invention, an amount of the Mo equivalent of the W compound typically employed in the synthesis can be used. Thus if the mixed metal oxide reaction involves compound WX then the skilled man can simply reduce the amount of WX and add an appropriate amount of MoX. For example $MoO_3$ can be employed instead of $WO_3$ and so on. The amount of Mo added is simply a reflection of the desired stoichiometry.

Manipulation of the stoichiometry is typically achieved by varying the amounts of starting material employed.

The mixed metal oxides of formula (II) of the invention can be prepared by a soft chemistry route, as described in US 2004/0241071 wherein the appropriate amounts of the binary oxides or carbonates or nitrates are dissolved. A citric acid sol-gel route is then applied which yields crystalline powders after calcination at elevated temperatures above 800° C.

Spinels of formula (IV) are generally readily available compounds which often occur naturally. Synthetic spinels of formula (IV) can be synthesized using the same methods described for the synthesis of rare-earth tungstates.

The solid phase material formed by these processes may need to be further manipulated to manufacture a membrane. Milling of these materials, where necessary, is achieved conventionally, e.g. using an agate mill and is typically carried out in alcohol, e.g. isopropanol. This is removed prior to a calcination step.

Calcination can take place at any useful temperature depending on the nature of the material, e.g. a temperature of from 800 to 1700° C. as is known in the art, e.g. 1000 to 1500° C. It is preferred if calcination is carried out until a single phase material is formed. This can be determined readily by X-ray diffraction analysis.

The powder can be pressed and sintered. Pressing and sintering can be carried out using known conditions. For example, pressing is typically carried out at ambient temperature in any standard press and sintering can occur at temperatures up to 1600° C., e.g. 800 to 1500° C., preferably 1000 to 1450° C., e.g. 1200° C. to 1400° C.

Powders formed by the processes above can be single phase and are typically submicron in size and non agglomerated. Post calcination particles sizes can be 10 to 1000 nm, preferably 100 to 800 nm, especially 200 to 600 nm in diameter.

The powders made by the processes defined above are then suitable for mixing to provide the composite conducting layer comprising a combination of a rare-earth tungstate and a mixed metal oxides. Mixing can be performed by milling the powders together, e.g. using an agate mill and is typically carried out in alcohol, e.g. ethanol. The powder is then dried and pressed into pellets. For membranes, particle size values are preferably 100-800 nm, especially 200-600 nm in diameter.

Membrane

The proton conducting membranes of the invention comprise a rare-earth tungstate of formula (I) as hereinbefore described combined with a mixed metal oxide of formula (II), (III) or (IV) as hereinbefore described, or mixtures thereof.

In all embodiments, it is preferred if the weight ratio of the rare-earth tungstate (I) to the mixed metal oxide(s) in the conducting layer is between 5:1 and 1:5, such as 3:1 to 1:3, preferably 2:1 to 1:2, especially about 1:1. The particle size of both components is preferably less than 5 microns, especially less than 1 micron.

The thickness of the conducting layer of the ceramic membrane of the invention can vary however it is preferred if it is less than 100 microns in thickness, such as less than 80 microns in thickness, especially less than 50 microns in thickness. It will be preferred if the membrane of the invention is gas impermeable after it has been sintered.

The proton conductivity of the membrane of the invention at 700° C. may be at least $1 \times 10^{-4}$ S/cm, such as $1 \times 10^{-3}$ S/cm, preferably at least $1.5 \times 10^{-3}$ S/cm, especially at least $2 \times 10^{-3}$ S/cm.

The membrane of the invention will preferably possess an electronic conductivity greater than about 0.01 S/cm, such as 0.1 S/cm, preferably at least 0.5 S/cm, especially at least 1 S/cm under reducing conditions and/or oxidizing conditions.

It will be appreciated that the electronic conductivity will vary depending on the conditions. The values above are preferably determined following the protocols in the examples.

It is preferred if the rare-earth tungstate of formula (I) and the mixed metal oxides of formula (III) have a fluorite type crystal structure. The mixed metal oxide of formula (II) preferably has a perovskite structure. The mixed metal oxide of formula (IV) has a spinel structure.

In all embodiments, it is further preferred if the conducting layer of the proton conducting membrane is coated on both sides with a porous electron conducting coating or dense hydrogen permeable coating. This coating preferably comprises a single phase material. The single phase material may be selected from a metal or metal-based alloy or ceramic compound. Examples of metals include Pt, Au, Ir, Ag or Ni, Pd. Examples of metal alloys include, PdAg or PdCu Examples of ceramic compounds include carbides such as $Mo_2C$ and oxides such as $Cr_2O_3$. Most preferably the single phase material is Ni or Pt. It is also preferable if the coating is catalytically active towards hydrogen dissolution or evolution.

The porous conducting coating preferably has a thickness of less than 10 microns, especially less than 6 microns, such as less than 4 microns. Grain size in the conducting coating is preferably less than 5 µm, especially less than 1 µm, such as less than 0.2 µm. The open porosity is preferably higher than 20%, especially higher than 30%, such as higher than 40%.

The porous electron coating acts as a catalyst and an electron collector and distributor. This helps to boost the electron distribution in the conducting layer.

In the simplest embodiment, the proton conducting membrane of the invention is self supported. A mixture of the rare-earth tungstate and mixed metal oxide, made as described above, can simply be employed as a membrane. It is preferred, however, if the membrane of the invention is multilayered and is formed from the conducting layer, a layer of the dehydrogenation catalyst and optionally a support layer. Preferably, the conducting layer has a porous electron conducting coating, as described above, on both sides.

The proton conducting membrane will typically be formed using a layer of rare-earth tungstate and mixed metal oxide having a thickness as described above. Altering the thickness of the proton conducting layer in the membrane can be used to adjust the selectivity of the reactor to protons.

The amount of catalyst, when present, i.e. the thickness of the catalyst layer, may vary between 50 µm to 1 mm, e.g. depending on the targeted temperature, pressure and yield.

Alternatively, the membrane can be formed simply from the conducting layer and optional support with the dehydrogenation catalyst forming, for example, a packed bed attached to the membrane.

Several thin film techniques can be used to deposit rare-earth tungstate and mixed metal oxide thin films so as to form the membrane of the invention. These include:
  Screen printing;
  Chemical vapour deposition techniques (CVD);
  Spray deposition methods—e.g. ultrasonic spray deposition (USD);
  Electrophoretic deposition;
  Spin and dip coating;
  Slurry coating; and
  Impregnation.

Screen printing, spray deposition and spin/dip coating are preferred techniques. Screen printing is easy to upscale and can readily achieve thicknesses down to 10 µm.

The membrane will preferably be formed as a planar membrane or tubular membrane.

In a planar embodiment the membrane is preferably deposited on a porous support using a screen printing technique.

There are various options for membrane formation and any method known in the art may be used. The rare-earth tungstate and mixed metal oxide can be pre-formed and then used to form a membrane or precursors to the mixed metal oxides can form a membrane with the final proton conducting membrane being formed upon calcination.

Thus, a homogeneous ink of the rare-earth tungstate and mixed metal oxide can be fabricated using suitable organic chemicals. The combined powders, made by the methods described above, can be formed into a stable suspension. One way of achieving that is to disperse the rare-earth tungstate and mixed metal oxide in a binder with dispersing agents. Binders include the mixture of terpineol/ethyl-cellulose and dispersing agents are oleic acid and solsperse 3000. It is important that the dispersing agent burns off at relatively low temperatures to avoid carbon residues in the sintered product. This will give a stable suspension of the rare-earth tungstate and mixed metal oxide powders.

The support can then be dipped, using dip-coating technique or the suspension is sprayed on the support using spray-coating technique, or the suspension is screen printed on the support, etc. The support-membrane assembly is then heat treated (150-400° C.) to ensure membrane to support binding.

In an alternative planar embodiment, the membrane can be deposited on the porous support using a spin coating technique. A homogeneous slurry of the rare-earth tungstate and mixed metal oxide can be made using suitable organic chemicals as described above. The slurry can then be deposited on the spinning support using spin coating apparatus. The thickness of the membrane film can be adjusted by the amount deposited and in addition the number of deposits. Between each deposit the membrane-support assembly can be dried to evaporate the volatile organic solvents. The membrane-support assembly is then fired to the desired sintering temperature, which can be tailored to the particle size.

For a tubular membrane, a preferred technique is deposition by spray coating. A stable suspension of the rare-earth tungstate and mixed metal oxide is sprayed on the tubular support utilizing spray coating apparatus, to a suitable membrane film thickness. The coated tubes are then heat treated to suitable sintering temperature.

Dip coating is a further option here. A suspension with desired wetting properties can be prepared and support tubes dipped in said suspension a selected number of times depending on the desired membrane film thickness with a drying stage in between each deposition. The membrane-support assembly can again be heat treated to suitable sintering temperature.

The skilled man is therefore able to prepare proton conducting membranes of the invention.

The principles of operation are not dependent on the structure of the reactor, and are therefore the same for a planar design and for a tubular design.

Membranes may need to be regenerated periodically. This can be achieved with oxygen flush.

Support

It may be necessary to use a membrane support to carry the conducting layer and/or catalyst. In some embodiments, the membrane of the invention is self supporting however, it is within the scope of the invention to use a support. The support should be inert, porous and capable of withstanding the conditions within the membrane reactor.

The following are important properties for the support:
  Porous
  Chemically compatible with the membrane—does not react to form a secondary insulating phase or with the gas environment at high temperatures, especially in the presence of water and $CO_2$;
  Mechanically compatible with the membrane—thermal expansion coefficient should preferably match that of the membrane.

The following are preferred properties of the support:
  Catalytically active towards the formation of water;
  Proton and electron conducting—to increase the number of triple phase boundaries where the formation of water take place;
  Graded porosity towards the membrane to ease the deposition of the dense membrane.

Typically the support will be an inert metal oxide such as an alkali metal oxide or silica or alumina. Such supports are well known in this field. Supports may be 200-300 μm to 1 mm or more in thickness.

The design of the support material depends on the design of the whole reactor. Typically the membrane, and hence any support, will be planar or tubular. The term tubular is used herein to designate a membrane is in the shape of a "test tube", i.e. a cylinder with hemispherical end portion but open at the other end.

In a tubular embodiment porous support tubes are extruded. The support is then heat treated to yield the desired mechanical strength. In a planar embodiment the support material can be tape casted, also followed by heat treatment to yield the desired mechanical strength. In a tape casting process, a slurry of the oxide is typically spread evenly onto a flat horizontal surface by means of a doctor blade. After drying, the thin film formed can be removed, cut to the desired shape and fired.

To manufacture a support structure either as a planar support or as a tube, an ink of the desired support material can be produced either using water as a solvent or an organic solvent, optionally as well as stabilizing agents. To have controlled porosity, a pore filler material is often used, e.g. carbon black. The ink can then be tape cast or extruded. The support is subsequently fired to a desired firing temperature, such as 600 to 1500° C. to yield mechanical robust supports with a desired porosity.

Reactor

The proton conducting membrane of the invention may be used in a proton conducting membrane reactor. By reactor is meant a vessel in which the process of the invention can be carried out. The membrane can consist of two or three parts, the support, the conducting layer and optionally the catalyst. The reactor comprises the membrane, the catalyst (if present and if that is not part of the membrane), and has a first zone and a second zone separated by the membrane formed from the conducting layer. A catalyst may not be needed, e.g. when the reactor is operated at high temperatures.

In the first zone, the substance to be dehydrogenated can in one embodiment be contacted with the dehydrogenation catalyst thus forming hydrogen and a dehydrogenated product. In a second embodiment the substance to be dehydrogenated is decomposed in the first zone thus forming hydrogen and a dehydrogenated product. The hydrogen passes through the proton conducting membrane but as this membrane is selective, the dehydrogenated product remains within the first zone and can be collected from the outlet of the first zone. It is not required to remove all the hydrogen produced in the first zone, although ideally a significant portion is removed to enable formation of the favourable product.

In the second zone, hydrogen which has passed through the membrane is normally oxidised to water by reaction with oxygen or converted to some other hydrogen containing compound in an oxidation reaction. Alternatively, an inert purge gas could be used to remove hydrogen or a partial vacuum can be applied in the second zone to reduce hydrogen content. The idea here is to reduce the hydrogen content in the second zone to create a concentration gradient for the hydrogen between first and second zones. As hydrogen is dragged from first to second zone, the hydrogen concentration in the first zone decreases thus encouraging dehydrogenation in the first zone.

Preferably a purge gas passes through the second zone. As noted above, the mixed metal oxide is stable in the presence of air so air can be used as the purge gas. This is attractive as air is free unlike the inert gases conventionally used in the art.

In the presence of air, the hydrogen reacts with oxygen to form water which can be removed.

The process takes place at a temperature of 300 to 1200° C., preferably 400 to 900° C. It is preferred that the reactor is at this temperature when the substance to be dehydrogenated is added.

Note that the reaction of oxygen and hydrogen is exothermic so control over temperature may be required. However, dehydrogenation reactions are often endothermic. The process of the invention is typically carried out at a temperature of 300 to 1200° C., preferably 400 to 900° C. which means that the heat generated by the reaction of hydrogen and oxygen can also be used to maintain the temperature within the reactor as a whole.

It is also possible to use elevated pressure in the process of the invention. This is attractive in the case of steam reforming where high water vapour pressure will increase the hydrogen permeability of the membrane itself as a result of increased hydration.

As an alternative to an oxygen containing gas or inert purge gas, the hydrogen could be removed using a partial vacuum.

The reactor will have an inlet and an outlet in both zones to allow reactants in and products/wastes out of the reactor.

The first zone will therefore comprise an inlet for the substance to be dehydrogenated and an outlet for the dehydrogenated product. It will be appreciated that some unreacted substance may also be removed and a separation of product/reactant may be required. Unreacted substance can of course be fed back to the reactor.

In some embodiments, the second zone will also have an inlet for purge gas and an outlet for removing purge gas and hydrogen/purge gas reaction products. Alternatively, the second zone may just have an outlet for removing hydrogen using a vacuum.

The skilled man will be able to devise reactor set ups to carry out the process herein.

Dehydrogenation Catalyst

The reactor of the invention should in a preferred embodiment comprise a dehydrogenation catalyst. The specific catalyst depends on the specific reaction for which the membrane reactor is to be used but can be readily selected by the person skilled in the art. The dehydrogenation catalyst can form part of the actual membrane or the catalyst could simply be present in the first zone of the reactor. The skilled man can devise any suitable arrangement to ensure that the catalyst performs its desired function.

The dehydrogenation catalyst catalyses the dehydrogenation of the substance of interest. The dehydrogenation catalyst is preferably a porous catalyst but it should ideally have some electron and proton conductivity as these species may need to be transported through the catalyst on the membrane.

Any dehydrogenation catalyst can be used as long as it is able to operate under the conditions of the reaction described in detail below. It will also be preferred if the dehydrogenation catalyst can function in the presence of acids and air. Ideally, the catalyst used is one for dehydrogenation of alkanes.

Suitable catalysts include oxides of the first row of transition metals such as Ni, Fe, Pt, Ag, Pd and their alloys. These can be supported on alkali metal oxides. Suitable examples are $Cr_2O_3$, $Al_2O_3$, $MoO_3$ and $V_2O_5$.

Some perovskite compounds may be suitable as catalysts such as those of formula $AB_{1-q}B'_qO_{3-z}$ where A=Ca, Sr or Ba; B=Ce, Tb, or Pr; B'=Ti, V, Cr, Mn, Fe, Co, Ni, or Cu or combinations thereof; and 0.02≤q≤0.5. The value of z ensures that the compounds are uncharged.

Preferably, however, the catalyst is a zeolite. Preferred zeolites are those having the structure TON and MTW. Specifically preferred structures are ZSM-22 and ZSM-12, e.g. ZSM-2 (MTW like).

Highly preferred zeolites are ZSM-5 zeolites, especially HZSM-5 zeolites, where the metal is Mo, W, Fe, V or Cr, listed starting with highest activity.

For methane dehydrogenation, the most preferred catalyst is a H-ZSM5 with an active metal with reported activity in the order Mo>W>Fe>V>Cr.

For ethane dehydrogenation preferred catalysts include alumina supported $Cr_2O_3$, $MoO_3$ and $V_2O_5$.

For dehydrogenation during steam reforming preferred catalysts include supported Ni.

The choice of metal depends on the design, the desired activity and the compatibility with the membrane reactor.

A catalyst can also be used in the second zone (reducing side) of the membrane, but this is not essential. This catalyst will aid conversion of hydrogen which passes through the membrane into water or other hydrogen sink.

Examples of such a catalyst are Ag, a lanthanum/cerium cobalt mixed metal oxide (e.g. $La_{1-q}Sr_qCoO_{3-z}$ where 0.2≤q≤0.5, z to balance) or a mixed metal cobalt oxide (e.g. $ACO_{1-q1}M_{q1}O_3$ where A=Ca, Sr and Ba, and M=Fe, Co and Ni where 0≤q1≤0.5).

These catalysts, typically in the form of powders, can be obtained commercially.

In one embodiment the catalyst will be deposited on the membrane. This will be achieved by techniques such as dip coating or impregnation, where the catalyst is dispersed in a solution. The membrane is then heat treated so that the catalyst is adhered to the membrane surface.

A second embodiment includes a reactor where the catalyst is freely lying on top of, or in front of the membrane. The catalyst can be in the form of powder with tailored particle size. The catalyst is not adhered to the membrane. In this embodiment the catalyst can therefore easily be exchanged if it needs to be regenerated externally.
Substance It is preferred if the compound for dehydrogenation is a hydrocarbon, especially a saturated hydrocarbon such as an alkane or cycloalkane. Especially preferably the alkane is a $C_{1-4}$ alkane, most especially methane (e.g. natural gas), ethane, propane or butane.

Methane is dehydrogenated according to the equation:

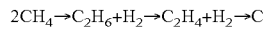

$$2CH_4 \rightarrow C_2H_6 + H_2 \rightarrow C_2H_4 + H_2 \rightarrow C$$

Using a Mo HZSM-5 catalyst, the mechanism of the reaction seems to involve the conversion of $CH_4$ to $C_2H_4$ on e.g. molybdenum carbide or oxycarbide and further conversion of $C_2H_4$ to aromatic products over the acidic sites within the channels of the zeolite.

It will be appreciated that the dehydrogenation reaction needs to be stopped before the formation of coke. This is achieved using a combination of factors such as the ideal conductivity of the membrane, and a suitable catalyst. Temperature and pressure can also be used to adjust the equilibrium of the above reaction.

It will also be appreciated that any alkene formed may dimerise or trimerise under the conditions in the reactor to form, for example benzene.

The conversion of substance achieved in this invention is preferably at least 95 wt %, preferably at least 97 wt %, e.g. 99 wt % or more. This means that almost all the substance (typically an alkane) fed to the reactor is converted to the dehydrogenated desired product (typically an alkene).

Moreover, it is preferred if the selectivity is preferably at least 95 wt %, preferably at least 97 wt %, e.g. close to 100 wt %. This means that the formed dehydrogenated product is at least 95 wt % pure, i.e. there are almost no impurities present at all.

It is also preferred if the compound of dehydrogenation is a mixture of alkanes and water as in steam reforming. Methane is steam reformed according to the following equation:

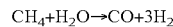

$$CH_4 + H_2O \rightarrow CO + 3H_2$$

Using a Ni-containing catalyst, the conversion is increased by removing hydrogen. The steam reforming reaction is endothermic, and heat can be supplied by heat transfer through the membrane from the exothermic reaction between permeated hydrogen and sweep air. The membrane enables heat management within the system.

Further, compared to using complex metal membranes or unstable perovskites of the prior art, the proton conducting membrane of this invention is stable even in chemically harsh conditions at high temperatures.

It is also envisaged that the membrane and reactor of the inventor could be used in the decomposition of hydrogen sulphide. The rare-earth tungstate and mixed metal oxides of the invention are stable in sulphur containing atmospheres, and are therefore ideal for use in $H_2S$ decomposition. Here, the catalyst used should be one that enables hydrogen sulphide decomposition such as thiospinels $AB_2S_4$ (where A is a 2+ group VIII ion and B is a 3+ group VIII ion e.g. $FeFe_2S_4$) or $WS_2$.

The invention will now be further described with reference to the following non limiting examples and Figures.

EXAMPLES

Figure 1:
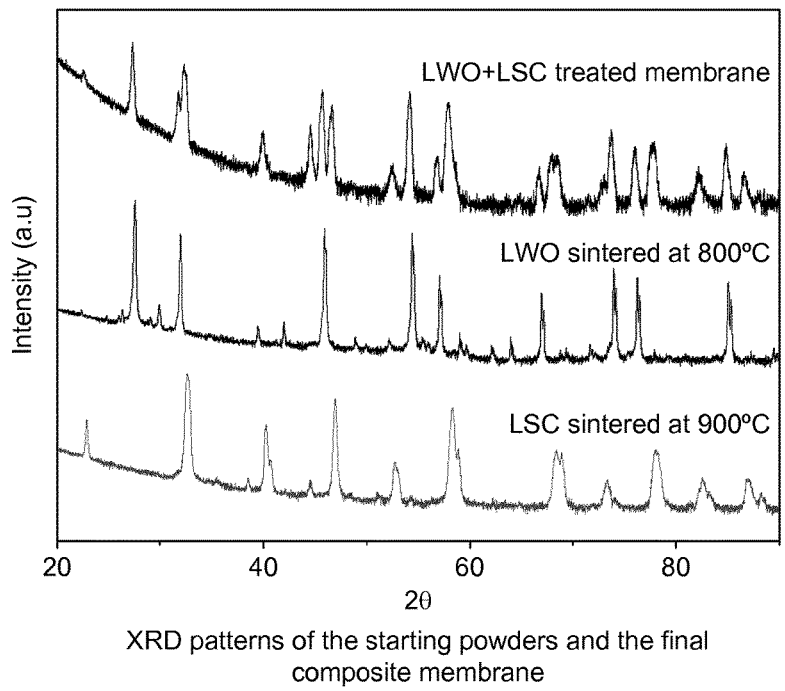
FIG. 1 shows XRD patterns of the starting powders and the final composite membrane.

Preparation of Materials
Preparation by Sol-Gel (Pechini Method)
Rare-Earth Tungstate [LWO]($La_{5.55}WO_{12-\delta}$)

The preparation method employed here is based on the citrate-complexation route. The lanthanum oxide was dissolved in concentrated hot nitric acid (65% vol.) in stoichiometric proportion and the resulting nitrate was complexed using citric acid at a molar ratio 1:2 cation charge to citric acid. Another solution was prepared for the B cations (purity>99%), using ammonium tungstate, and complexing it with citric acid (Fluka, 99.5%) at the same ratio. Metal complexation in both cases was promoted by heat treatment at 120° C. for 1 hour. Both solutions were neutralized by controlled addition of ammonium hydroxide (32% wt.) and mixed at room temperature. The resulting solution was gradually concentrated by stepwise heating under stirring up to 150° C. and followed by foaming. The resulting product was subsequently calcined in air to eliminate carbonaceous matter and to promote mixed oxide crystallization. The final materials were annealed at 800° C.

Mixed Metal Oxide [LSC]($La_{0.85}Sr_{0.15}CrO_{3-\delta}$)

The preparation method was similar to that employed for LWO. In this case Sr carbonate and Cr(VI) oxide were used as starting compounds. The final sintering temperature was 800° C.

For the composite preparation, LSC and LWO powder were ball milled together in a 1:1 wt ratio in ethanol for 8 hours and then the dried powder was pressed into pellets.

X-Ray Diffraction and SEM Technique

XRD was carried out on a Philips X'Pert Pro equipped with a X'celerator detector using monochromatic Cu $K_\alpha$ radiation. XRD patterns were recorded in the 2θ range from 20° to 90° and analyzed using X'Pert Highscore Plus software (PANalytical).

The microstructure of the composite membranes was analyzed by scanning electron microscopy (SEM-EDS) in a JEOL JSM6300 electron microscope.

Hydrogen Permeation Test Procedure

The composite membrane used in hydrogen permeation measurements consisted of a gastight 700-400 μm thick disc with diameter 15 mm sintered at 1550° C. Both disk sides were coated by screen printing with a 20 μm layer of a Pt ink (Mateck, Germany) in order to improve the catalytic activity of the sample.

Permeation measurements were performed on a double chamber quartz reactor. Hydrogen (100 mL/min) was separated from a mixture of $H_2$—He (dry or saturated in water at 25° C.) using argon as sweep gas (150 mL/min). Feed and sweep humidification was accomplished by saturation at 20° C. using Milli-Q water. From the hydrogen content measured in the argon side (permeate side) and the argon flow rate, the total hydrogen permeation rate was calculated, assuming ideal gas law. The permeation fluxes (mL·min$^{-1}$·cm$^{-2}$) were calculated by dividing the permeation rates by the effective surface area of the membranes. The hydrogen content in the permeate side was analyzed using micro-GC Varian CP-4900 equipped with Molsieve5A, PoraPlot-Q glass capillary, and CP-Sil modules. Qualitative analysis of water concentration is done in the PoraPlot-Q channel. Sealing was done using gold rings and an acceptable sealing was achieved when the helium concentration was lower than 5% of the $H_2$ permeated. Data reported were achieved at steady state after thirty minutes of stabilization and each test was repeated at least three times to minimize analysis error, obtaining an experimental standard deviation of $10^{-4}$.

Conductivity Measurement Procedure

Standard four-point DC conductivity measurements were carried out as a function of temperature for 4 different environments: dry $H_2$, $H_2+H_2O$ (2.5% vol.), dry $D_2$ and $D_2+D_2O$ (2.5% vol.), where hydrogen and deuterium are diluted in He (95%). A constant current was supplied by a programmable current source (Keithley 2601) while the voltage drop through the sample was detected by a multimeter (Keithley 3706).

Results

XRD

The compatibility of both oxidic phases after sintering of the membrane was evaluated by XRD diffraction and the results are shown in FIG. 1. The XRD patterns confirm good mixing.

SEM

Figure 2:
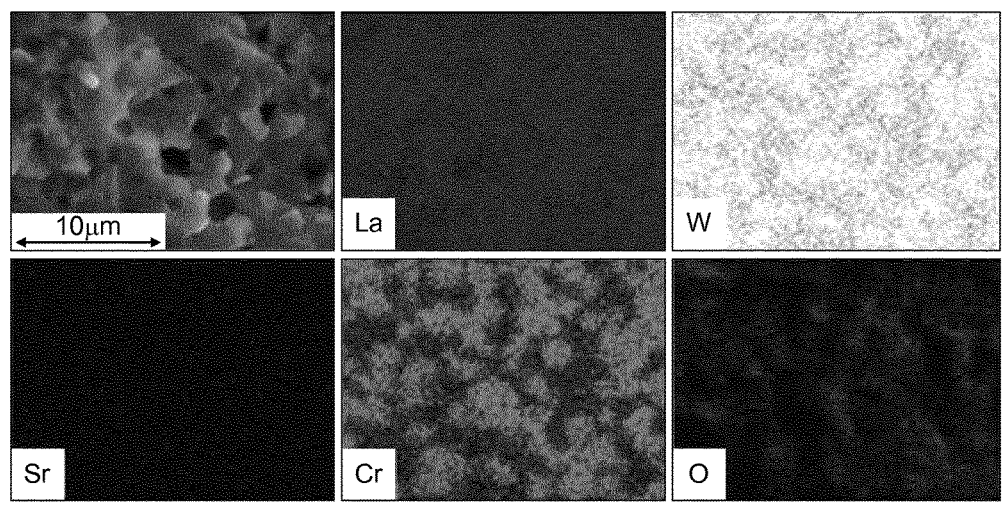
FIG. 2 is a SEM image and EDX analysis of a 50/50 composite membrane.
Figure 3:
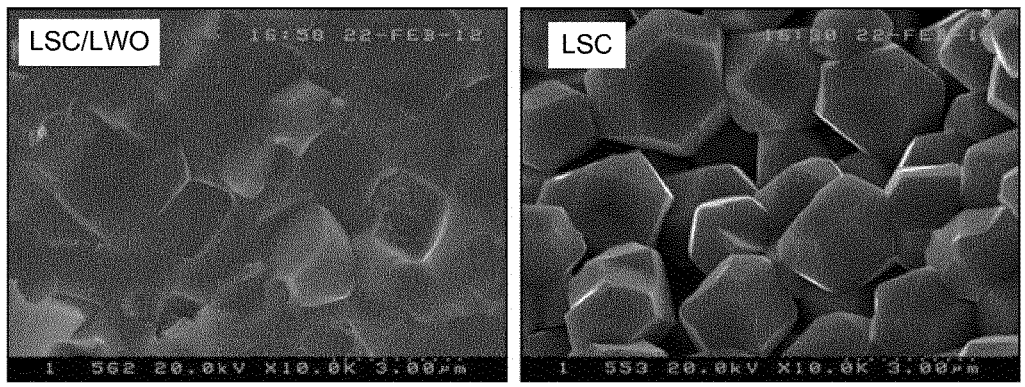
FIG. 3 is a SEM images of a 50/50 composite membrane and a LSC membrane.

Mixing of the two metal oxides phases was also evaluated by SEM analysis performed on a 50/50 composite membrane (FIG. 2). FIG. 3 presents the SEM analysis of a LWO/LSC composite membrane compared with an all-LSC membrane, both sintered at 1550° C. The grains in the composite membrane have an average grain size around 2 μm, while the grains are well-sintered and the remaining porosity is negligible. In the case of the all-LSC membrane (FIG. 3, right-hand image), the membrane porosity is still very high due to the low sintering activity of LSC.

Figure 4:
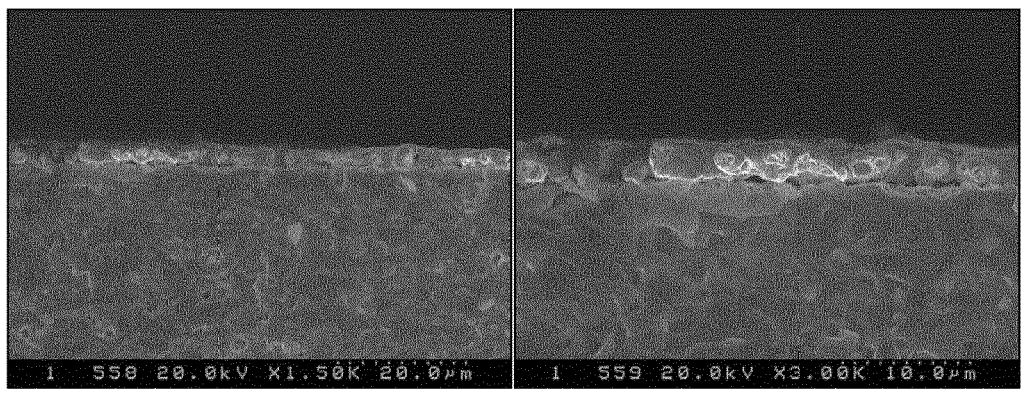
FIG. 4 is a SEM image of a 50/50 composite membrane with the top electronic coating.
Figure 5:
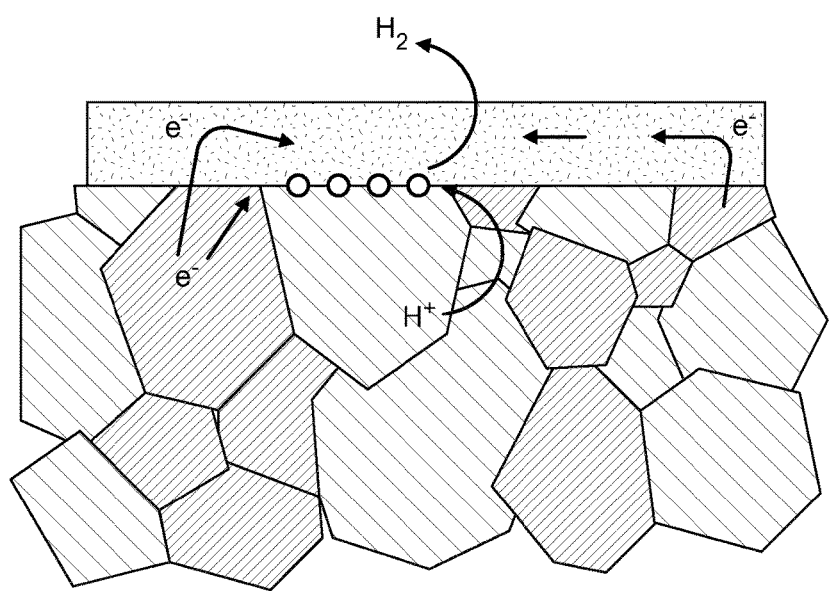
FIG. 5 is a schematic illustration of membrane operation of the composite membrane coated with a top porous electronic layer.

SEM analysis was then repeated following deposition of a porous platinum layer on both sides of the membrane. The SEM images are shown in FIG. 4. The layer was around 2-3 μm-thick and continuous along the composite membrane surface. As a result, the entire surface of the LWO grains was connected/contacted to/with the porous Pt coating, which acts as catalyst and an electron collector/distributor. Indeed, the whole LWO surface is connected to the electron percolating LSC phase through the top porous coating. FIG. 5 is a schematic representation of the role of the electronic coating in the function of the membranes of the invention.

Conductivity Results

Figure 6:
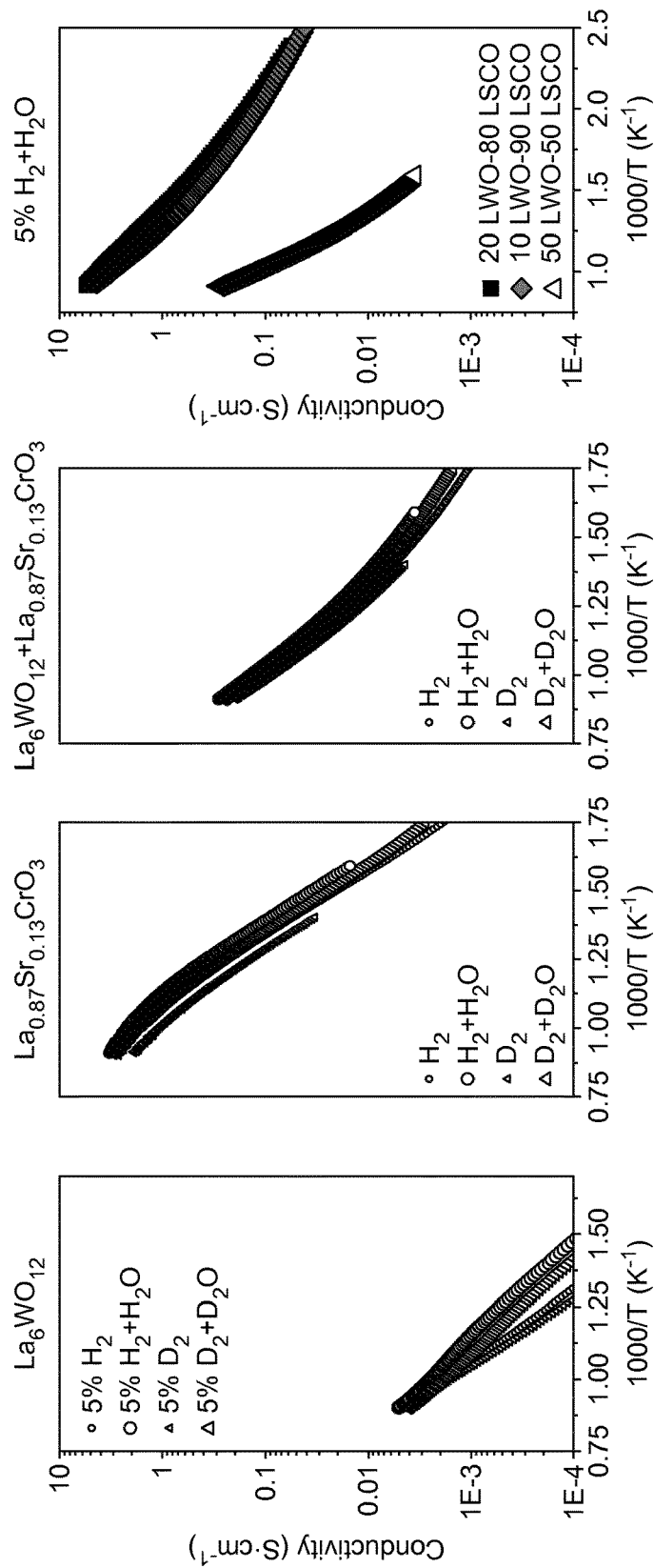
FIG. 6 shows a total conductivity of LWO, LSC and different LWO-LSC composites as function of inverse temperature measured under four different reducing atmospheres.

Total conductivity measurements for LWO, LWO+LSC (50/50 composite) and LSC are presented in FIG. 6 as a function of inverse temperature in $H_2$, $D_2$, $H_2+H_2O$ and $D_2+D_2O$ (where $H_2$ and $D_2$ are diluted (5%) in helium (95%) and $pH_2O$ and $pD_2O$ are 0.025 atm) atmospheres. In the case of LWO, proton transport prevails up to 800° C. as can be deduced from the hydration effect ($\sigma_{H_2+H_2O}>\sigma_{H_2}$ and $\sigma_{D_2+D_2O}>\sigma_{D_2}$) and the isotopic effect ($\sigma_{H_2+H_2O}>\sigma_{D_2+D_2O}$). However, at higher temperatures, both n-type and oxygen-ion conduction prevail with respect to proton conduction (as discussed in Solis C., Escolástico S., Haugsrud R., Serra J. M., J. Phys. Chem. C 115 (2011) 11124-11131). P-type conductivity is reported to prevail in LSC in the whole temperature range measured. When looking at the conductivity results, the expected p-type behavior is observed, which is related to the variation of pO2 when hydrogen is humidified, however this behavior is very similar to the one of pure proton conductors (hydration effect and the isotopic effect—see San Ping Jiang, Li Liu, Khuong P. Ong, Ping Wu, Jian Li, Jian Pu. Electrical conductivity and performance of doped $LaCrO_3$ perovskite oxides for solid oxide fuel cells, Journal of Power Sources 176 (2008) 82-89) and no clear conclusions can be extracted with regard to the proton conducting character of LSC. The same behavior as for LSC can be observed in the 50/50 composite conductivity results, which appears to be principally a p-type electronic conductor; however the magnitude of the gas humidification and the isotopic effect are lower than in LSC. In summary, the total conductivity of the composite is 10 times lower than LSC but it is 2 orders of magnitude higher than LWO. The effect of the proportion between LWO and LSC phases on the total conductivity is shown in FIG. 6 (right-hand chart).

Hydrogen Permeation

Thickness of Membrane and Ratio of Components

Figure 7:
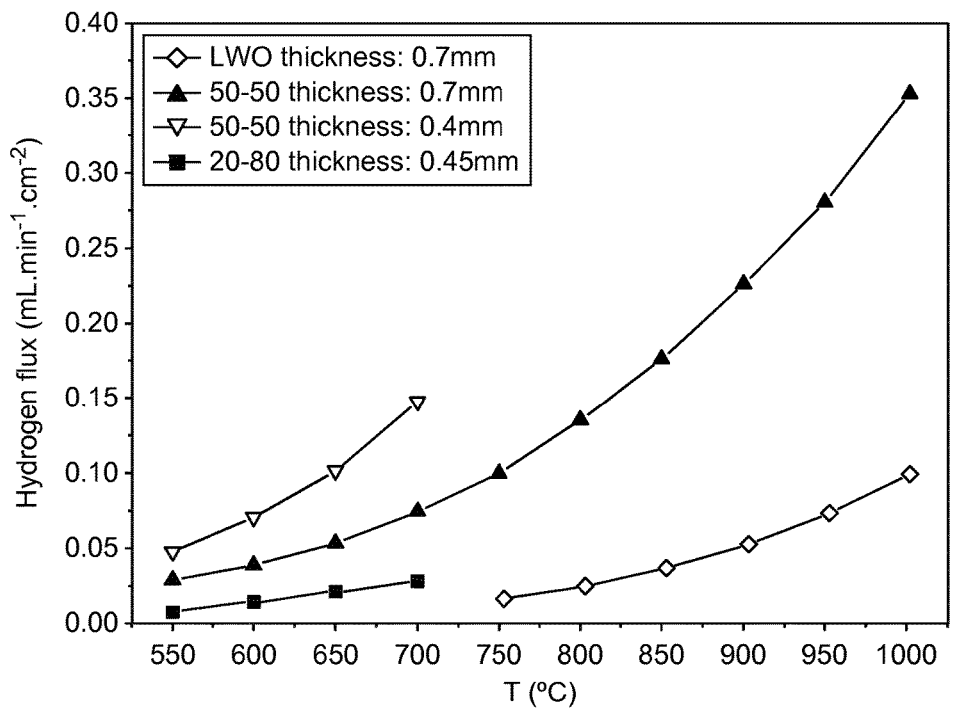
FIG. 7 shows the hydrogen separation flow obtained with three different kinds of membranes.

The effect of blending the LWO and LSC phases on hydrogen permeation/separation was investigated. Membranes with a porous electron conducting coating were used. Results are shown in FIG. 7. At 750° C., the 50/50 composite membrane (0.7 mm-thick) achieves hydrogen fluxes around 0.1 ml/min*cm$^2$ while the all-LWO membrane (0.7 mm-thick) exhibits a flow around 0.015 ml/min*cm$^2$. The enhancement in hydrogen permeation observed is considered to be due to the improvement in electron percolation by adding both (i) a mostly electronic conducting phase (LSC) and (ii) a "current distributor" coating on both membrane sides.

The effect of the LWO/LSC ratio in the membrane on hydrogen flux was also investigated at 700° C., where proton transport is the prevailing mechanism. The 50/50 composite membrane (0.4 mm-thick) achieves hydrogen fluxes around 0.15 ml/min*cm$^2$ while the 20/80 LWO/LSC composite membrane (0.4 mm-thick) exhibits a flow around 0.025 ml/min*cm$^2$ despite the much higher total conductivity observed for this composite (FIG. 6). This result suggests that (1) the proton percolation in LSC is lower than in LWO; (2) there exists an optimum ratio between LWO and LSC, which would also depend on the microstructure.

Figure 8:
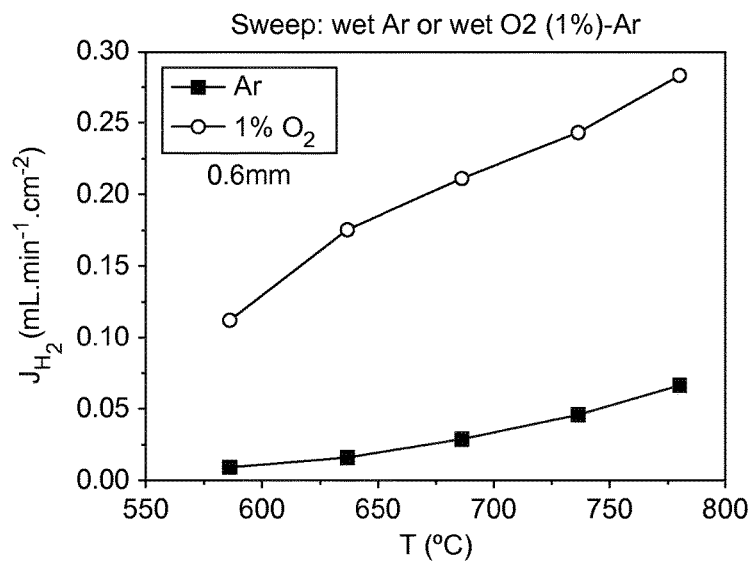
FIG. 8 shows hydrogen flux as a function of temperature using wet Ar and wet 1% $O_2$ diluted with Ar as sweep gas.

To investigate the effect of the chemical potential gradient, flux was monitored using 1% wet $O_2$ as sweep gas. The results are given in FIG. 8 where it is also compared using wet Ar as sweep gas. The hydrogen flux increases approximately 5 times moving to oxidizing sweep conditions. This confirms that the electronic conductivity in the LWO/LSC is p-type in the whole $pO_2$ range and that air can be used as sweep gas to obtain an increase in chemical potential gradient and a corresponding increase in hydrogen flux.

An 100% LSC membrane was not tested since it was not possible to achieve high density membranes (leak-free) even after sintering at very high temperatures, which is thought to be due to the low LSC sintering activity and the associated chromium evaporation.

Humidification and Temperature

Figure 9:
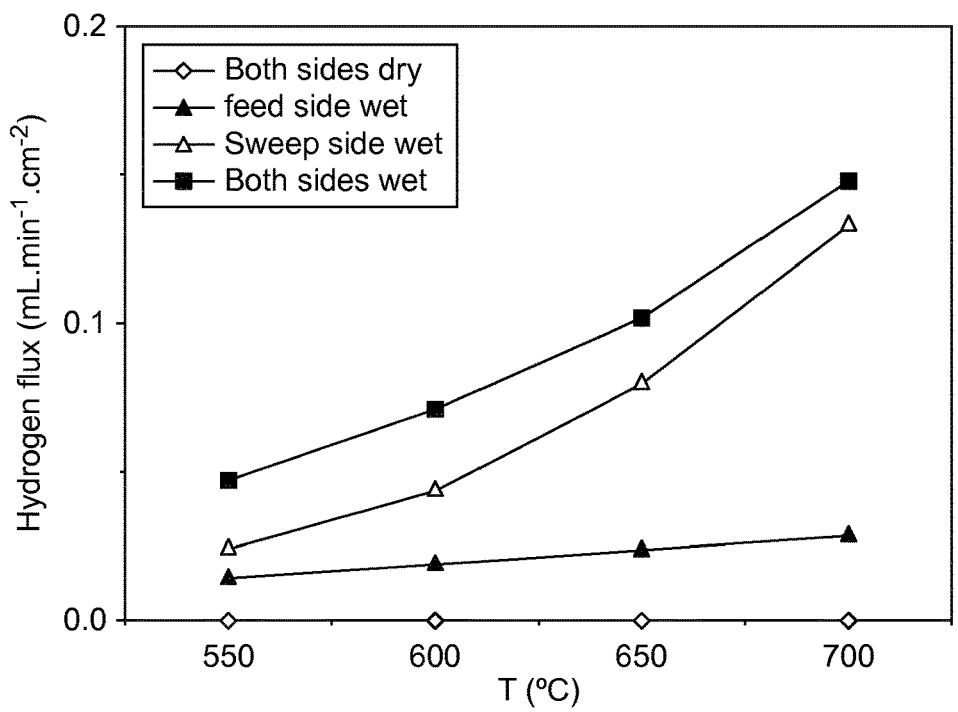
FIG. 9 shows a "Low" temperature permeation test using a 0.4 mm-thick membrane, best composite composition.
Figure 9:
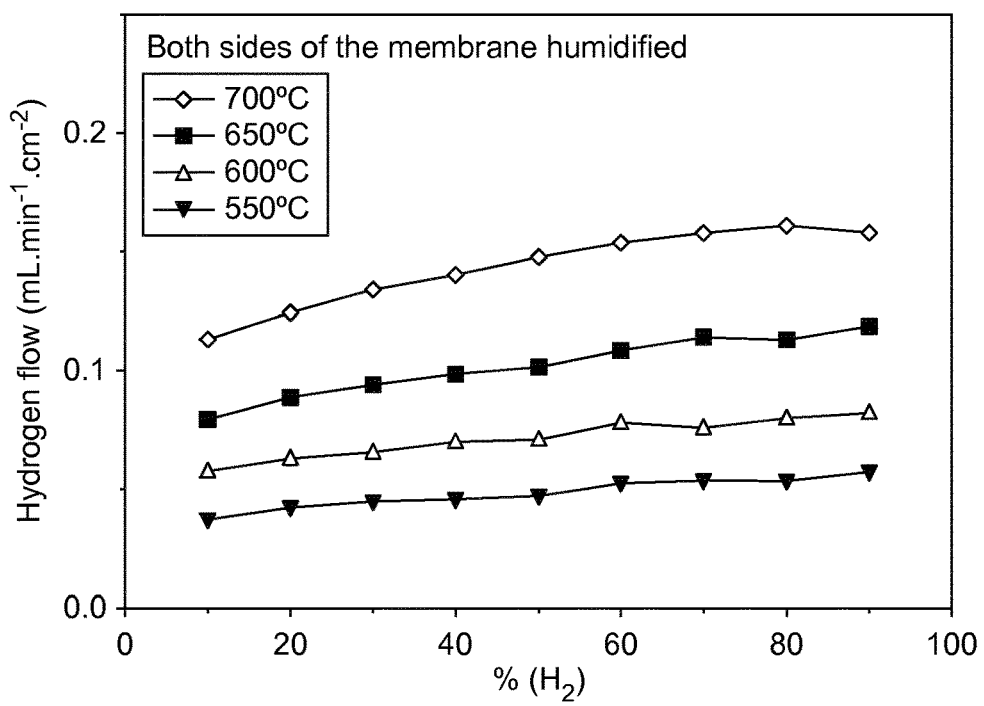

The best performing membrane (50/50 LWO/LSC) was further investigated for effects of humidification and temperature on hydrogen permeation. The results are shown in FIG. 9. The left-hand chart shows the effect of the humidification of sweep and feed stream. Having both sides of the membrane wet optimised hydrogen flux. Steam permeation is still relevant although proton transport is the prevailing mechanism. The right-hand chart illustrates the effect of the hydrogen concentration (in He) in the low temperature range. Flux was highest at 700° C.

$CO_2$ Atmosphere

Figure 10:
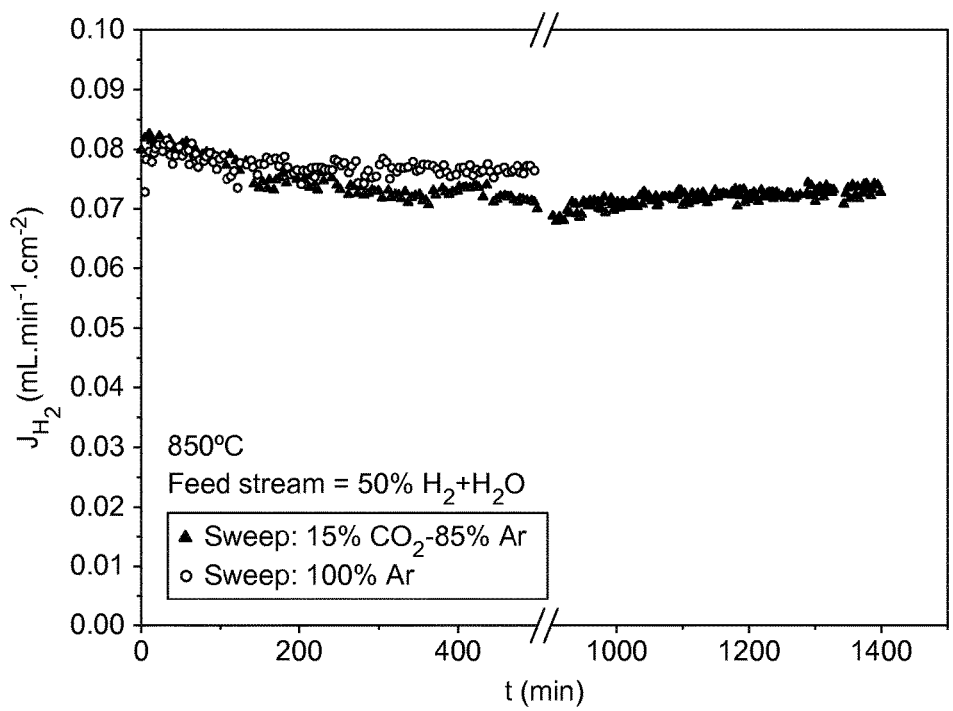
FIG. 10 shows the stability on stream in $CO_2$ environment (0.7 mm-thick 50/50 composite membrane): Hydrogen flow as function of time using 15% CO2-85% Ar as sweep gas and 50% He-50% $H_2$ as feed gas at 800° C.; both sides of the membrane were humidified.

Hydrogen permeation measurements were performed using 15% $CO_2$ in Ar as sweep gas. The measurements were carried out at 800° C. during 3 days using as feed gas 50% $H_2$ in helium and both sides of the membrane were humidified. FIG. 10 shows hydrogen flow under these conditions as a function of time and it can be observed that hydrogen permeation is stable in $CO_2$ atmospheres. The value of the hydrogen flow is slightly lower as compared with the case of using pure Ar as sweep gas, which is ascribed to competitive adsorption effects on the membrane/catalyst surface between $CO_2$, $H_2$ and $H_2O$.

Figure 11:
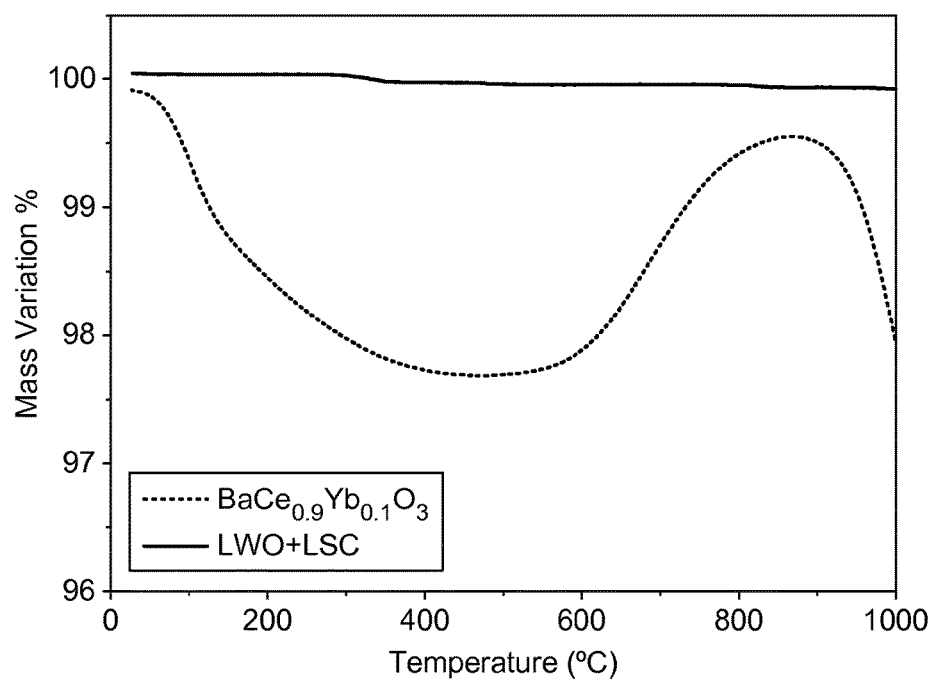
FIG. 11 shows TG measurements of LWO+LSC cer-cer in 5% $CO_2$ in Ar.

Other stability tests were carried out and showed the high stability of LSC/LWO composites even in $CO_2$ (FIG. 11) and $CO_2$+$H_2S$+HCN-containing wet environments.

Porous Coating

Figure 12:
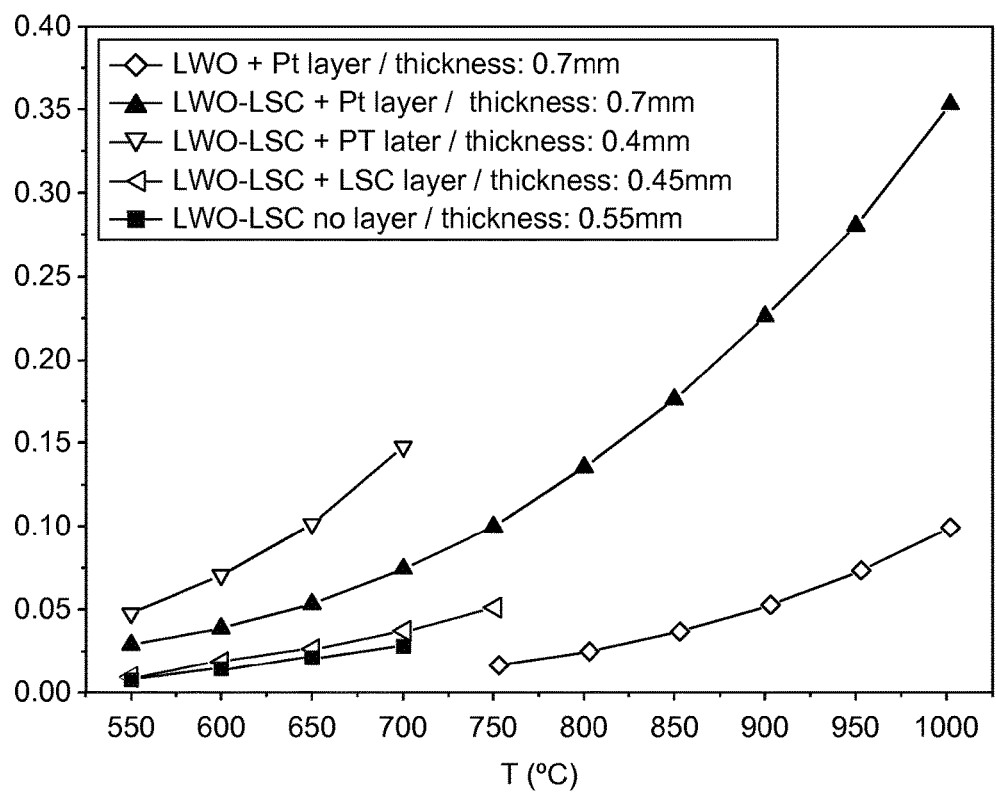
FIG. 12 shows the hydrogen separation flow obtained with three different kinds of membranes.

FIG. 12 shows the permeation results for 50/50 composite membrane with different coatings and thickness. The best result is obtained when the membrane is coated with a porous Pt coating. The lack of a porous electronic-conducting coating reduces substantially the permeation while the application of LSC porous coating improves slightly the permeation of the bare composite membrane.

The invention claimed is:

1. A proton conducting ceramic membrane comprising a conducting layer, wherein said conducting layer comprises a mixture of:

(i) a rare-earth tungstate of formula (I)

$$(Ln_{z1}Dp_{z2})_a W_{b-c} M1_c O_{12-y} \quad (I)$$

wherein

Ln is Y, an element numbered 57 to 71, or a mixture thereof;

Dp is Y or an element numbered 57 to 71 of the periodic table different from Ln;

Z1 is 0.5 to 1;

Z2 is 0.5 to 0;

M1 is a metal selected from the group consisting of Mo, Re, V, Cr, Nb, U and Mn, or a mixture thereof;

the molar ratio of a:b is 4.8 to 6;

c is 0 to (0.5*b); and y is 0≤y≤1.8 and is a number such that formula (I) is uncharged; and (ii) a mixed metal oxide of formula (II)

$$Ln_{e-d} M3_d Cr_{1-f} M2_f O_{3-x} \quad (II)$$

wherein

Ln is Y, an element numbered 57 to 71, or a mixture thereof;

M3 is a metal selected from Ca, Sr or Ba;

M2 is a metal selected from the group consisting of Al, Ga, Co, Ti, Mg, Mn, Fe, Ni, Y, Sc, Yb and Lu, or a mixture thereof;

e is 0.95 to 1;

d is 0.4 to 0.01;

f is 0 to 0.5; and x is 0≤x≤0.5 and is a number such that formula (II) is uncharged.

2. A membrane as claimed in claim 1, wherein the rare-earth tungstate (i) is of formula (I')

$$La_a W_{b-c} Mo_c O_{12-y} \quad (I')$$

wherein the molar ratio of a:b is 4.8 to 6;

c is 0 to (0.5*b); and y is a number such that formula (I) is uncharged and y is 0≤y≤1.8.

3. A membrane as claimed in claim 1, wherein the mixed metal oxide (ii) is of formula (II')

$$Ln_{e-d} Sr_d CrO_{3-x} \quad (II')$$

wherein

Ln is Y, an element numbered 57 to 71, or a mixture thereof;

e is 0.95 to 1;

d is 0.4 to 0.01; and x is a number such that formula (II) is uncharged and x is 0≤x≤0.5.

4. A membrane as claimed in claim 1, wherein the membrane is coated on both sides with a porous electron conducting coating or a dense hydrogen permeable coating.

5. A membrane as claimed in claim 4, wherein the porous electron conducting coating is a single phase material selected from a metal, metal-based alloy or a ceramic compound.

6. A membrane as claimed in claim 4, wherein the porous electron conducting coating is Ni or Pt.

7. A membrane as claimed in claim 4, wherein the porous conducting coating has a thickness of less than 10 microns.

8. A membrane as claimed in claim 1, wherein the conducting layer is less than 100 microns in thickness.

9. A membrane as claimed in claim 1, wherein the ratio of component (i) to component (ii) is about 1:1.

10. A membrane as claimed in claim 1, wherein the particle size of components (i) and (ii) is less than 5 microns.

11. A proton conducting membrane reactor comprising a dehydrogenation catalyst and a proton conducting membrane as defined in claim 1.

12. A reactor comprising a first zone comprising a dehydrogenation catalyst and a second zone separated from said first zone by a proton conducting membrane as defined in claim 1.

13. A process for the dehydrogenation of substance, comprising introducing said substance into the first zone of a reactor as defined in claim 12 thereby dehydrogenate said substance;
 allowing hydrogen formed during said dehydrogenation to pass through said proton conducting membrane into said second zone;
 introducing a purge gas into said second zone, to react with the hydrogen; or
 applying reduced pressure in said second zone to thus remove hydrogen from said second zone.

* * * * *